United States Patent
Menger et al.

(10) Patent No.: US 6,377,042 B1
(45) Date of Patent: Apr. 23, 2002

(54) METHOD AND APPARATUS FOR MERGING OF NMR ECHO TRAINS IN THE TIME DOMAIN

(75) Inventors: Stefan K. Menger, Exton; Manfred G. Prammer, Downingtown, both of PA (US)

(73) Assignee: NUMAR Corporation, Malvern, PA (US)

( * ) Notice: Subject to any disclaimer, the term of this patent is extended or adjusted under 35 U.S.C. 154(b) by 0 days.

(21) Appl. No.: 09/371,767

(22) Filed: Aug. 10, 1999

Related U.S. Application Data

(60) Provisional application No. 60/098,596, filed on Aug. 31, 1998.

(51) Int. Cl.⁷ .................................................. G01V 3/00
(52) U.S. Cl. ...................................................... 324/303
(58) Field of Search ......................................... 324/303

(56) References Cited

U.S. PATENT DOCUMENTS

| | | |
|---|---|---|
| 1,158,959 A | 11/1915 | Beach |
| 2,912,641 A | 11/1959 | Ruble |
| 2,973,471 A | 2/1961 | Armistead et al. |
| 3,205,477 A | 9/1965 | Kalbfell |
| 3,213,357 A | 10/1965 | Brown et al. |
| 3,360,716 A | 12/1967 | Bloom et al. |
| 3,395,337 A | 7/1968 | Varian |
| 3,402,344 A | 9/1968 | Brown et al. |
| 3,453,433 A | 7/1969 | Alger et al. ............... 250/83.3 |
| 3,508,438 A | 4/1970 | Alger et al. .................. 73/152 |
| 3,567,935 A | 3/1971 | Nagel ........................ 250/83.1 |
| 3,567,936 A | 3/1971 | Tittman ..................... 350/83.1 |
| 3,590,228 A | 6/1971 | Burke .................... 235/151.35 |
| 3,593,116 A | 7/1971 | Culpepper ..................... 324/5 |
| 3,617,867 A | 11/1971 | Herzog ........................... 324/5 |
| 3,638,484 A | 2/1972 | Tixier ........................... 72/152 |
| 3,657,730 A | 4/1972 | Robinson et al. ............... 324/5 |

(List continued on next page.)

FOREIGN PATENT DOCUMENTS

| | | | |
|---|---|---|---|
| EP | 0 295 134 A2 | 12/1988 | ............ G01V/3/32 |
| EP | 0 581 666 A3 | 2/1994 | ............ G01V/3/32 |
| EP | 0 649 035 B1 | 4/1995 | ............ G01V/3/32 |
| GB | 2 056 082 | 7/1980 | .......... G01N/24/08 |
| WO | WO 92/10768 | 6/1992 | ............ G01V/3/32 |
| WO | WO 98/25164 | 6/1998 | ............ G01V/3/32 |

(List continued on next page.)

OTHER PUBLICATIONS

Dunn et al., "A method for Inverting NMR Data Sets with Different Signal to Noise Ratios", paper JJ presented at the 39th Annual logging symposium of the Society Professional Well Log Analysts, Keystone, May 26–29, 1998.*

(List continued on next page.)

*Primary Examiner*—Christine Oda
*Assistant Examiner*—Tiffany A. Fetzner
(74) *Attorney, Agent, or Firm*—Pennie & Edmonds LLP

(57) ABSTRACT

Proposed is a new method and system to obtain enhanced-resolution NMR data by merging, in the time domain, different NMR pulse echo trains into a single echo train. The input echo trains can be acquired with different inter-echo spacing, wait time, and signal-to-noise ratio parameters that are optimized to correspond to both fast and slow portions of the $T_2$ spectrum. The merged echo trains are inverted into complete $T_2$ spectra in a single step thereby overcoming ambiguities and other limitations of prior art methods. In a preferred embodiment the merging process does not require a priori information about $T_1$, and the merged echo trains are optimized in with respect to $T_2$ resolution. The method of this invention is preferably practiced with the latest generation of multi-volume NMR logging tools, that allow simultaneous recordation of NMR data with different inter-echo spacing $T_e$, wait time $T_w$, and signal-to-noise ratio (SNR) parameters.

44 Claims, 12 Drawing Sheets

U.S. PATENT DOCUMENTS

| | | | |
|---|---|---|---|
| 3,667,035 A | 5/1972 | Slichter | 324/5 R |
| 3,777,560 A | 12/1973 | Guignard | 73/151.5 |
| 3,784,898 A | 1/1974 | Darley et al. | 324/5 R |
| 3,896,668 A | 7/1975 | Anderson et al. | 73/152 |
| 4,291,271 A | 9/1981 | Lauffer | 324/307 |
| 4,310,887 A | 1/1982 | Suau | 364/422 |
| 4,350,955 A | 9/1982 | Jackson et al. | 324/303 |
| 4,479,564 A | 10/1984 | Tanguy | 181/105 |
| 4,528,508 A | 7/1985 | Vail, III | 324/303 |
| 4,536,714 A | 8/1985 | Clark | 324/338 |
| 4,629,986 A | 12/1986 | Clow et al. | 324/303 |
| 4,656,422 A | 4/1987 | Vail, III et al. | 324/303 |
| 4,686,364 A | 8/1987 | Herron | 250/256 |
| 4,710,713 A | 12/1987 | Taicher et al. | 324/303 |
| 4,714,881 A | 12/1987 | Givens | 324/303 |
| 4,717,876 A | 1/1988 | Masi et al. | 324/303 |
| 4,717,877 A | 1/1988 | Taicher et al. | 324/303 |
| 4,717,878 A | 1/1988 | Taicher et al. | 324/303 |
| 4,728,892 A | 3/1988 | Vinegar et al. | 324/309 |
| 4,785,245 A | 11/1988 | Lew et al. | 324/308 |
| 4,792,757 A | 12/1988 | Vail, III et al. | 324/303 |
| RE32,913 E | 4/1989 | Clark | 324/338 |
| 4,825,163 A | 4/1989 | Yabusaki et al. | 324/318 |
| 4,829,252 A | 5/1989 | Kaufman | 324/309 |
| 4,875,013 A | 10/1989 | Murakami et al. | 324/318 |
| 4,885,540 A | 12/1989 | Snoddy et al. | 324/318 |
| 4,899,112 A | 2/1990 | Clark et al. | 324/338 |
| 4,933,638 A | 6/1990 | Kenyon et al. | 324/303 |
| 4,933,640 A | 6/1990 | Kuckes | 324/339 |
| 4,949,045 A | 8/1990 | Clark et al. | 324/338 |
| 4,987,368 A | 1/1991 | Vinegar | 324/303 |
| 4,994,777 A | 2/1991 | Leupold et al. | 335/302 |
| 5,023,551 A | 6/1991 | Kleinberg et al. | 324/303 |
| 5,055,787 A | 10/1991 | Kleinberg et al. | 324/303 |
| 5,055,788 A | 10/1991 | Kleinberg et al. | 324/303 |
| 5,122,746 A | 6/1992 | King et al. | 324/307 |
| 5,138,263 A | 8/1992 | Towle | 324/338 |
| 5,200,699 A | 4/1993 | Baldwin et al. | 324/303 |
| 5,212,447 A | 5/1993 | Paltiel | 324/300 |
| 5,235,285 A | 8/1993 | Clark et al. | 324/342 |
| 5,280,243 A | 1/1994 | Miller | 324/303 |
| 5,309,098 A | 5/1994 | Coates et al. | 324/303 |
| 5,349,184 A | 9/1994 | Wraight | 250/266 |
| 5,350,925 A | 9/1994 | Watson | 250/269.3 |
| 5,359,324 A | 10/1994 | Clark et al. | 340/854.3 |
| 5,363,041 A | 11/1994 | Sezginer | 324/303 |
| 5,376,884 A | 12/1994 | Sezginer | 324/303 |
| 5,379,216 A | 1/1995 | Head | 364/422 |
| 5,381,092 A | 1/1995 | Freedman | 324/303 |
| 5,387,865 A | 2/1995 | Jerosch-Herold et al. | 324/303 |
| 5,397,989 A | 3/1995 | Spraul et al. | 324/321 |
| 5,412,320 A | 5/1995 | Coates | 324/303 |
| 5,432,446 A | 7/1995 | Macinnis et al. | 324/303 |
| 5,453,692 A | 9/1995 | Takahashi et al. | 324/318 |
| 5,486,761 A | 1/1996 | Sezginer | 324/303 |
| 5,486,762 A * | 1/1996 | Freedman et al. | 324/303 |
| 5,497,087 A | 3/1996 | Vinegar et al. | 324/303 |
| 5,498,960 A | 3/1996 | Vinegar et al. | 324/303 |
| 5,517,115 A | 5/1996 | Prammer | 324/303 |
| 5,557,200 A | 9/1996 | Coates | 324/303 |
| 5,557,201 A | 9/1996 | Kleinberg et al. | 324/303 |
| 5,565,775 A | 10/1996 | Stallmach et al. | 324/303 |
| 5,629,623 A | 5/1997 | Sezginer et al. | 324/303 |
| 5,680,043 A | 10/1997 | Hurlimann et al. | 324/303 |
| 5,705,927 A | 1/1998 | Sezginer et al. | 324/303 |
| 5,757,186 A | 5/1998 | Taicher et al. | 324/303 |
| 5,767,674 A | 6/1998 | Griffin et al. | 324/303 |
| 5,796,252 A | 8/1998 | Kleinberg et al. | 324/303 |
| 5,923,167 A | 7/1999 | Chang et al. | 324/303 |
| 6,005,389 A * | 12/1999 | Prammer | 324/303 |
| 6,023,163 A * | 2/2000 | Flaum et al. | 324/303 |
| 6,049,205 A * | 4/2000 | Taicher et al. | 324/303 |

OTHER PUBLICATIONS

Prammer et al., "Measurements of Clay–Bound Water and Total Porosity by Magnetic Resonance Logging", paper SPE 36522 presented at the 71st Annual Technical Conference and Exhibition of the society of Petroleum Engineers, Denver, Oct. 6th–9th, 1996.*

Menger S. and Prammer M. "A New Algorithm for Analysis of NMR Logging Data" paper SPE 49013 accepted for the 73rd Annual Technical Conference and Exhibition of the Society of Petroleum Engineers, New Orleans, Sep. 27th–30th, 1998.*

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Carr et al., "Effects of Diffusion on Free Precision in Nuclear Magnetic Resonance Experiments," *Physical Review,* vol. 94. No. 3 (May 1, 1954), pp. 630–638.

*Schlumberger Wireline & Testing,* "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRIL Show—A New Approach to 'Formation Factor,'" National SPWLA Convention (Jun. 15, 1992), pp. 1–15.

Kleinberg et al., "Novel NMR Apparatus for Investigating an External Sample," *Journal of Magnetic Resonance,* (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservoir Sandstones," *Society of Petroleum Engineers* (1990), pp. 733–741.

Miller et al., "Spin Echo Magnetic Resonance Logging: Porosity and Free Fluid Index Determination," *Society of Petroleum Engineers,* SPE 20561 (1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

*Schlumberger Technology News—Oilfield Bulletin,* "Fifth Generation Nuclear Magnetic Resonance Logging Tool: A Major Advance in Producibility Measurement Technology," (Jul. 1995) (2 pp.)

Akkurt et al., "NMR Logging of Natural Gas Reservoirs," SPWLA 36th Annual Logging Symposium (Jun. 26–29, 1995).

Prammer, M.G., "NMR Pore Size Distributions and Permeability at the Well Site," *Society of Petroleum Engineers,* SPE 28368, (1994) pp. 55–64.

Chandler et al., "Improved Log Quality with a Dual–Frequency Pulsed NMR Tool," *Society of Petroleum Engineers,* (1994) pp. 23–35.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "A NMR Technique for the Analysis of Pore Structure: Application to Materials with Well-Defined Pore Structure," Journal of Colloid and Interface Science, vol. 119, No. 1, Sep. 1987, pp. 127–140.

Neuman et al., "Applications of Nuclear Magnetism Logging to Formation Evaluation," Journal of Petroleum Technology, vol. 34, (1982) pp. 2853–2862.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Jackson et al., "Western Gas Sands Project Los Almos NMR Well Logging Tool Development," Los Alamos National Laboratory (Oct. 1981–Sep. 1982)pp. 1–28.

Clavier et al., "Theoretical and Experimental Bases for the 'Dual Water' Model for the Interpretation of Shaly Sands," *Journal of Petroleum Technology* (Apr. 1984), pp. 3–15.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15 (1979) No. 2, pp. 195–260.

Brownstein et al., "Importance of classical diffusion in NMR studies of water in biological cells," The American Physical Society, vol. 19, No. 6, (1979) pp. 2446–2453.

Farrar et al., "Pulse and Fourier Transform NMR Introduction to Theory and Methods," Academic Press (1971) pp. 26–29.

Waxman et al., "Electrical Conductivities in Oil-Bearing Shaly Sands," *Society of Petroleum Engineers Journal* (1968) pp. 107–122.

Brown et al., "Nuclear Magnetism Logging," Transactions of the Institute of Mining, Metallurgical, and Petroleum Engineers, vol. 219 (1960), pp. 199–207.

Akkurt et al., "Selection of Optimal Acquisition Parameters for MRIL Logs," SPWLA 37th Annual Logging Symposium, Jun. 16–19, 1996. Class 324/303.

Hou et al., "Nuclear Magnetic Resonance Logging Methods for Fluid Typing," Society of Petroleum Engineers, Inc., SPE 48896, 1998. Class 324/303.

Prammer et al., "Measurements of Clay–Bound Water and Total Porosity by Magnetic Resonance Logging," Society of Petroleum Engineers, SPE 36522, 1996.

Prammer et al., "Theory and Operation of a New, Multi-Volume, NMR Logging System," SPWLA 40th Annual Logging Symposium, May 30–Jun. 3, 1999.

Nascimento et al., "Anomalous NMR Responses in Highly Permeable Sandstone Reservoirs: A Case Study," SPWLA 40th Annual Logging Symposium, May 30–Jun. 3, 1999.

Cannon et al., "Quantitative NMR Interpretation," Society of Petroleum Engineers, SPE 49010, 1998.

Chen et al., "Estimation of Hydrocarbon Viscosity with Multiple TE Dual Wait–Time MRIL Logs," Society of Petroleum Engineers, SPE 49009, 1998.

Freedman et al., "Combining NMR and Density Logs for Petrophysical Analysis in Gas–Bearing Formations," SPWLA 39th Annual Logging Symposium, May 26–29, 1998.

Singer et al., "Fast NMR Logging for Bound Fluid and Permeability," SPWLA 38th Annual Logging Symposium, Jun. 15–18, 1997.

Edwards et al., "Effects of Tool Design and Logging Speed on $T_2$ NMR Log Data," SPWLA 38th Annual Logging Symposium, Jun. 15–18, 1997.

Kleinberg et al., "Nuclear Magnetic Resonance of Rocks: $T_1$ vs. $T_2$," Society of Petroleum Engineers, SPE 26470, 1993, pp. 553–563.

Prammer et al., "A New Multiband Generation of NMR Logging Tools," Society of Petroleum Engineeers, SPE 49011, 1998.

Herrick et al., "An Improved Nuclear Magnetism Logging System and its Application to Formation Evaluation," Society of Petroleum Engineers, SPE 8361, 1979.

Clavier et al., "Theoretical and Experimental Bases for the Dual–Water Model for Interpretation of Shaly Sands," Society of Petroleum Engineers Journal, 1984, pp. 153–168.

Coates et al., "A New Approach to Improved Log–Derived Permeability," SPWLA Fourteenth Annual Logging Symposium, May 6–9, 1973, pp. 1–27.

Jasper A. Jackson, "Nuclear Magnetic Resonance Well Logging," The Log Analyst, Sep.–Oct., 1984, pp. 16–30.

Kleinberg et al., "NMR Properties of Reservoir Fluids," The Log Analyst, Nov.–Dec. 1996, pp. 20–32.

Coates et al., "The Magnetic Resonance Imaging Log Characterized by Comparison With Petrophysical Properties and Laboratory Core Data," Society of Petroleum Engineers, SPE 22723, 1991, pp. 627–635.

Hull et al., "Field Examples of Nuclear Magnetism Logging," Journal of Petroleum Technology, 1960, pp. 14–22.

Setser et al., "Measurement of Remaining Oil Saturation in Northern Michigan Using Nuclear Magnetism Log Data and Pressure Core," Society of Petroleum Engineers, SPE 14276, 1985.

Tang et al., LP–ZOOM a Linear Prediction Method for Local Spectral Analysis of NMR Signals, Journal of Magnetic Resonance 79, 190–196 (1988).

Chen et al., "Improving the Accuracy of NMR Relaxation Distribution Analysis in Clay–Rich Reservoirs and Core Samples," paper SCA 9702, in 1997 international symposium proceedings: Society of Professional Well Log Analysts, Society of Core Analysts Chapter–at–large, p. 10, 1997. Class 324/303.

Dunn et al., "A Method for Inverting NMR Data Sets With Different Signal to Noise Ratios," SPWLA 39th Annual Logging Symposium, May 26–29, 1998. (Class 324/303).

Menger et al., "A New Algorithm for Analysis of NMR Logging Data," Society of Petroleum Engineers, Inc., SPE 49013, 1998.

Coates et al., "Applying NMR Total and Effective Porosity to Formation Evaluation," Society of Petroleum Engineers, Inc., SPE 38736, 1997.

Edwards et al., "Improved NMR Well Logs From Time–Dependent Echo Filtering," SPWLA 37th Annual Logging Symposium, Jun. 16–19, 1996.

* cited by examiner

METHOD AND APPARATUS FOR MERGING OF NMR ECHO TRAINS IN THE TIME DOMAIN

This application claims the benefit of U.S Provisional Application No. 60/098,596 filed Aug. 31, 1998.

FIELD OF THE INVENTION

The present invention relates to nuclear magnetic resonance (NMR) logging, and more particularly to a method and system for processing different signals in the time domain to obtain a composite signal that is optimized in terms of its transform domain resolution.

BACKGROUND OF THE INVENTION

Nuclear magnetic resonance (NMR) logging has become an important input to formation evaluation in hydrocarbon exploration and is one of the preferred methods for determining formation parameters. Improvements in hardware as well as advances in data analysis and interpretation allow log analysts to generate detailed reservoir description reports, including clay-bound and capillary-bound related porosity, estimates of the amounts of bound and free fluids, fluid types (i.e., oil, gas and water), as well as permeability, based on NMR logs.

The basic input for analysis of NMR data are spectra of the transversal NMR relaxation time $T_2$ calculated from pulse-echo trains. Several issues arise in this context, and are considered in some detail next.

$T_2$ resolution $T_2$ resolution is affected by several parameters of the echo train, including the inter-echo spacing, echo train length and the noise.

Generally, the temporal length of the echo trains determines the maximum $T_2$ that can be resolved. FIG. 1 shows the normalized error between an input model and a $T_2$ inversion result as a function of echo train length, and in particular indicates the longest resolvable $T_2$ component as a function of the echo train length. The solid line shows the exact modeling results, while the dashed line represents the trend. The results were modeled using a Monte Carlo method, the noise standard deviation was σ=1 p.u. FIG. 1 suggests that the longest resolvable $T_2$ component is on the order of 2–3 times the length of the echo train. This is indicated in the figure by a sharp increase of the normalized error for $T_2$/echo-train-length ratio>2. Theoretically, Whittall et al. (see the reference below) have found that the "resolving power" of the echo train is proportional to $$SNR \cdot \sqrt{Ne} \quad (1)$$

where SNR is the signal-to-noise ratio of the signal and Ne is the number of echoes. FIG. 1 in combination with Eq. (1) indicates that the echo train length ($T_e \cdot Ne$) has a stronger influence on the longest $T_2$ that can be resolved than the noise.

Further modeling results support the assumption that noise is critical for the resolution of fast $T_2$ components. FIG. 2 shows the normalized error between fast $T_2$ components (0.5 to 3 ms) and the input model as a function of noise. The inter-echo spacing $T_e$ is 0.6 ms, σ ranges from 0.1 to 10 p.u. As expected, the uncertainty in determining fast $T_2$ components increases with the amount of noise.

Another aspect to consider is the ability to resolve fast $T_2$ components with respect to inter-echo spacing $T_e$. The modeling results are presented in FIG. 3. The noise standard deviation is σ=1 p.u. The normalized error is shown as a function of the fastest $T_2$ component normalized by $T_e$. The fastest $T_2$ component, which can be resolved, is on the order of the inter-echo-spacing $T_e$. Note that this holds true only if the first echo (recorded after one $T_e$-time) is included in the inversion. The results presented above allow the following conclusions:

(1) The resolution of fast $T_2$ components depends both on $T_e$ and noise. Low noise on the early echoes is as important as a small $T_e$ to obtain accurate short $T_2$'s; and (2) The temporal echo train length is the limiting factor for the resolution of long $T_2$ relaxation times. Noise does not play such an important role.

Note that all results were calculated using the fast $T_2$ inversion technique introduced by Prammer (MAP ALGORITHM (see reference to paper SPE 28368 below). It is expected that other inversion techniques will produce similar results.

Noise Optimization

Edwards and Chen suggested to improve the accuracy of results from NMR well logs by time-dependent filtering of echo train data. (see reference to paper RR below). They recommend applying a relatively weak filter on early echoes and gradually increasing the filter strength for later echoes. The results outlined above indicate that no significant improvement in $T_2$ resolution will be achieved by filtering.

Other methods, such as "windowing techniques" suffer from similar limitations. In order to preserve the information contents of the early echoes (yielding fast $T_2$ components), the window length for the early echoes has to be very short. Since a window length of 2 would effectively double the minimal $T_2$ component, a common practice is to set the window length to 1 for the first echoes, i.e., use the early echoes instead of windows. This highlights the importance of recording good, low noise, early echoes in the first place. With a multi-volume tool this can be done efficiently by stacking, while single volume tools need to sacrifice logging speed.

Prammer et al. introduced a technique, originally designed for a dual-volume NMR logging tool, to record low noise pulse-echo data. (See reference to Prammer et al., paper SPE 36522 below). The method allows to acquire pulse-echo NMR data covering the entire geologically meaningful $T_2$ range (approximately between 0.5 ms and 2 sec.) with adequate resolution and precision at acceptable logging speeds.

Essentially, two sets of data are recorded (quasi) simultaneously. One data stream consists of short stacked, low noise, echo trains with $T_e$=0.6 ms. The second data set includes long echo trains. It is recognized in the art that the early echoes of a CPMG pulse-echo data are significant for the determination of fast $T_2$ components. Slow $T_2$ components on the other hand can only be resolved with long echo trains.

The method involves recording blocks of short, under-polarized echo trains resolving the fast relaxation components $T_2$, interleaved with long, fully polarized echo trains that allow the determination of slow components. The two echo trains are analyzed separately and the partial spectra are combined to obtain a complete spectrum. This technique, developed for NUMAR Corporation's (a Halliburton Company) dual-volume tool (MRIL® C/TP*), allows acceptable logging speeds, while acquiring NMR logs of good quality. For a more detailed discussion of the method, the reader is directed to application Ser. No. 08/816,395 filed Mar. 13, 1997 to one of the co-inventors of this application, which is hereby incorporated by reference for all purposes. Extending the effective range of $T_2$ measurements using multiple quasi-simultaneous measurements represents an important advancement of the art.

It should be noted that while the wait time Tw between two long data sets is sufficiently long to fully polarize the hydrogen atoms, the 0.6 ms data used in the Prammer et al. method is recorded with a wait time of about Tw=20 ms. Thus the long components in the 0.6 ms data are not fully polarized. Hence the two data sets are inverted into $T_2$ domain separately. (See reference to paper SPE 36522 below).

In a separate step the two partial spectra are combined into one spectrum covering the full $T_2$ range. Although this method provides good results in most cases, the choice of the "combining point" of the two input spectra introduces some uncertainty. (See the references to Chen et al., paper SCA 9702; and Dunn et al., paper JJ cited below).

Another set of issues is presented by the latest generation of NMR logging tools (MRIL® Series D to NUMAR Corporation, a Halliburton company) that extend the concept of combining different echo trains and provide further analysis flexibility. These multi-volume instruments allow to simultaneously record NMR data with different inter-echo spacing $T_e$, wait time $T_w$, and signal-to-noise ratio (SNR). Each part of the data set can emphasize different NMR properties. That way, almost universal data can be acquired in single-pass operation. The problem then remains how to combine data sets in efficient and statistically meaningful ways that enhance the performance of the logging tools.

One approach is suggested in the Prammer et al. method considered above, where to obtain the complete $T_2$ spectra, different kinds of echo trains (i.e., short high-precision echo trains recorded with a short wait time $T_w$, and long echo trains with long $T_w$) are inverted in two sets of $T_2$. The first set covers fast $T_2$, while the second set resolves medium and long $T_2$. In a subsequent step the two partial spectra are concatenated. Notably the combination of different $T_2$ information is carried out in the $T_2$ domain.

Several authors (see the Chen and Georgi, paper SCA 9702; Dunn et al., paper JJ; references cited below) pointed out shortcomings of this method: (a) The "concatenation point" of the $T_2$ spectra is a source of uncertainty; (b) Straight $T_2$ spectra concatenation, i.e., without interpolation or tapering, can introduce artifacts into the final result; (c) $T_2$ spectra concatenation does not take into account any SNR difference between the two input spectra; (d) Other information embedded in the echo trains such as the longitudinal NMR relaxation time $T_1$ is ignored.

Chen and Georgi tried to minimize some of the uncertainty of $T_2$ spectra concatenation by calculating the clay bound water related porosity (CBW) from a partially recovered echo train. A back-transformed echo train representing the CBW porosity is then subtracted from a fully recovered echo train. They invert the correct echo train and merge the spectra (from partial recovered and fully recovered data) in the $T_2$ domain. This approach is limited in that: (a) The method is based on the assumption that all clay bound water is polarized in the partial recovered data. While this is true for most situations, examples have been found where this is not the case; (b) The "concatenation point" of the $T_2$ spectra is still a source of uncertainty; (c) The method does not take into account any SNR difference between the two input data sets.

Dunn et al. (see the list of references below) suggested a method to simultaneously invert two echo trains recorded with different $T_w$ into the $T_2$ domain. The proposed Composite-Data-Processing (CDP) method solves a linear equation system simultaneously for the two different echo trains in a least square sense. The CDP method has other limitations, including: (a) It requires a priori information about $T_1$; (b) In their implementation of CDP, Dunn et al. assume a constant $T_1$, which is not necessarily the case; (c) The difference in SNR between the two input echo trains is not exploited. Notably, the CDP does not merge echo trains. The combination of different $T_2$ information is rather done in an "equation domain".

Further background information on these issues can be found in the following references, the content of which is hereby incorporated by reference for all purposes.

1. Prammer, M. G., Drack, E. D., Bouton, J. C., Gardner, J. S., Coates, G. R., Chandler, R. N., Miller, M. N.: "Measurements of Clay-Bound Water and Total Porosity by Magnetic Resonance Logging", paper SPE 36522 presented at the $71^{st}$ Annual Technical Conference and Exhibition of the Society of Petroleum Engineers, Denver, Oct. 6–9, 1996.
2. Prammer, M. G.: "NMR Pore Size Distribution and Permeability at the Well Site", paper SPE 28368 presented at the $69^{th}$ Annual Technical Conference and Exhibition of the Society of Petroleum Engineers, New Orleans, Sept. 25–28, 1994.
3. Chen, S., Georgi, D. T.: "Improving the Accuracy of NMR Relaxation Distribution Analysis in Clay-Rich Reservoirs and Core Samples", paper SCA 9702, in 1997 international symposium proceedings: Society of Professional Well Log Analysts, Society of Core Analysts Chapter-at-large, p. 10, 1997.
4. Dunn, K-J., Bergman, D. J., LaTorraca, G. A., Stonard, S. M., Crowe, M. B.: "A Method for Inverting NMR Data Sets with Different Signal To Noise Ratios", paper JJ presented at the $39^{th}$ Annual Logging Symposium of the Society of Professional Well Log Analysts, Keystone, May 26–29, 1998.
5. Menger, S., Pranmner, M.: "A New Algorithm for Analysis of NMR Logging Data", paper SPE 49013 accepted for the $73^{rd}$ Annual Technical Conference and Exhibition of the Society of Petroleum Engineers, New Orleans, Sep. 27–30, 1998.
6. Coates, G. R., Menger, S., Prammer, M., Miller, D.: 'Applying NMR Total and Effective Porosity to Formation Evaluation', paper SPE 38736 presented at the $72^{nd}$ Annual Technical Conference and Exhibition of the Society of Petroleum Engineers, San Antonio, Oct. 5–8, 1997.
7. Chandler, R. N., Drack, E. D., Miller, M. N., Prammer, M. G.:"Improved Log Quality with Dual-Frequency Pulsed NMR Tool", paper SPE 28365 presented at the $69^{th}$ Annual Technical Conference and Exhibition of the Society of Petroleum Engineers, New Orleans, Sept. 25–28, 1994.
8. Whittal, K. P., Bronskill, M., Henjelman, R. M.: 'Investigation of Analysis Techniques for Complicated NMR Relaxation Data', J. Magn. Reson., 95, 221, 1991.
9. Edwards, C. E., Chen, S.: 'Improved NMR Well Logs from Time-Dependent Echo Filtering', paper RR presented at the $37^{th}$ Annual Logging Symposium of the Society of Professional Well Log Analysts, New Orleans, Jun. 16–19, 1996.

Additionally, collecting NMR data, constructing uni-exponential and multi-exponential models, and other NMR signal processing is known in the art and is described, for example, in U.S. Pat. Nos. 5,212,447; 5,280,243; 5,309,098; 5,412,320; 5,517,115; 5,557,200, and 5,696,448 to the assignee of the present application, as well as, application Ser. No. 08/816,395 filed Mar. 13, 1997 to one of the co-inventors of this application, which are hereby incorporated by reference for all purposes.

SUMMARY OF THE INVENTION

In view of the shortcomings of the prior art briefly summarized above, it is apparent that there is a need for a method and system that can take full advantage of the flexibility provided by current-generation NMR tools and enable the calculation of high-resolution $T_2$ spectra of the input signal over the entire geologically meaningful range of values. It is thus an object of the present invention to provide such a method and system that obviate problems associated with the prior art.

In particular, in accordance with the present invention a new method is proposed that allows to merge echo trains acquired with different parameters, comprising inter-echo spacing, wait time, and signal-to-noise ratio into one single echo train. In accordance with this invention, the merging is carried out in the time-domain. Amplitude correction is applied to adjust the value of partially recovered echo trains to fully recovered trains. A priori information about $T_1$, if available, can be used to make this adjustment directly. However, a priori information about $T_1$ is not required, because it may be extracted using the method of this invention. The merged echo train obtained in accordance with the present invention is optimized with respect to $T_2$ resolution. As a result of the application of the novel method, the complete $T_2$ spectrum can be calculated in a single step, with good resolution over its entire range of values.

To overcome limitations of the prior art methods used to compute complete $T_2$ spectra, in accordance with the present invention it is proposed to merge echo trains in the time domain, i.e., to merge different echo trains. In a preferred embodiment, the input echo trains can be acquired with different $T_e$, $T_w$, and SNR using, for example, NUMAR's MRIL® tool, D series. By combining two or more echo trains with different $T_e$ and signal-to-noise ratios, a single resulting echo train can be obtained, which is optimized in terms of $T_2$ resolution. This echo train serves as input for $T_2$ inversion algorithms, that can handle echo trains with different $T_e$ and SNR, such as the MAP algorithm (see Prammer et al., paper SPE 28368). In accordance with a preferred embodiment, if the input echo trains are acquired with $T_w$ too short to allow the protons to filly polarize (i.e., with partial recovery), the respective amplitude is adjusted to match the fully recovered echo data. The amount of amplitude adjustment provides information about the $T_1$ relaxation time.

More specifically, in accordance with the present invention, a method for conducting NMR logging measurements is disclosed, comprising: (a) providing at least one first echo train acquired using a first set of echo train parameters, said first echo train carrying information about relatively fast-relaxation NMR signals; (b) providing at least a second echo train acquired using a second set of echo train parameters, said second echo train carrying information about relatively slow-relaxation NMR signals; and (c) merging said at least one first and said at least one second echo trains in the time domain to obtain a merged echo train carrying information about both relatively fast and relatively slow NMR signals. In a specific embodiment, the first echo train(s) correspond to partially recovered NMR signals, and the second echo train(s) correspond to fully recovered NMR signals. In this embodiment, the method further comprises adjusting the amplitude of said partially recovered NMR signals to the amplitude of said relatively slow-relaxation NMR signals, where the adjustment can be performed in the time domain, and may take into account information about the $T_1$ spectrum of the signal.

In another aspect, the invention is a method for conducting NMR logging measurements with enhanced transform domain resolution, comprising: providing two or more NMR echo trains, each of said echo trains having parameters selected to cover a portion of the $T_2$ spectrum; combining said two or more NMR echo trains in the time domain into a merged echo train; and inverting the merged echo train to the $T_2$ spectrum domain to obtain information about the properties of an underlying material. In a specific embodiment, at least one of the two or more NMR echo trains corresponds to partially recovered NMR signals and at least one of the two or more NMR echo trains corresponds to fully recovered NMR signals, in which case the amplitude of the partially recovered NMR signals are preferably adjusted to the amplitude of the fully recovered NMR signals. In an important aspect of the invention, at least two of the two or more NMR echo trains are acquired quasi-simultaneously. In another important aspect, at least two of the two or more NMR echo trains are acquired in different sensitive volumes.

In another aspect, the invention is a method of operating a multi-volume NMR logging tool, comprising: (a) acquiring a first NMR echo train or sets of echo trains in a first sensitive volume of the tool, said first echo train(s) carrying information about relatively fast-relaxation NMR signals; (b) acquiring a second NMR echo train or sets of echo trains in a second sensitive volume of the tool, said second echo train(s) carrying information about relatively slow-relaxation NMR signals; and (c) merging said first and said second echo train(s) in the time domain to obtain a merged echo train carrying information about both relatively fast-relaxation and relatively slow-relaxation NMR signals. In a specific preferred embodiment, the first echo train(s) and said second echo train(s) are acquired quasi-simultaneously.

DETAILED DESCRIPTION OF THE INVENTION

Figure 1:
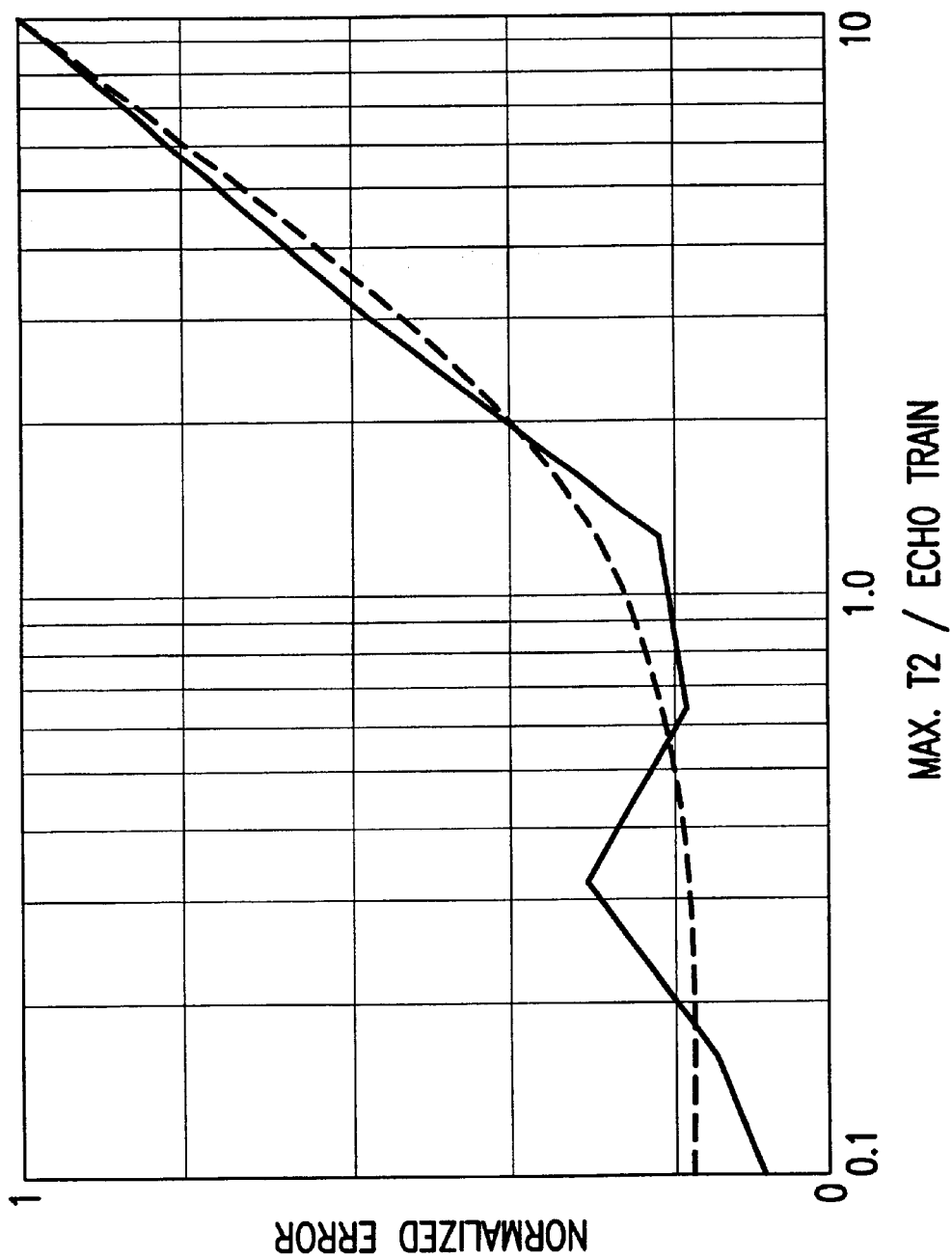
FIG. 1 shows the normalized error between an input model and $T_2$ inversion result as a function of echo train length.
Figure 2:
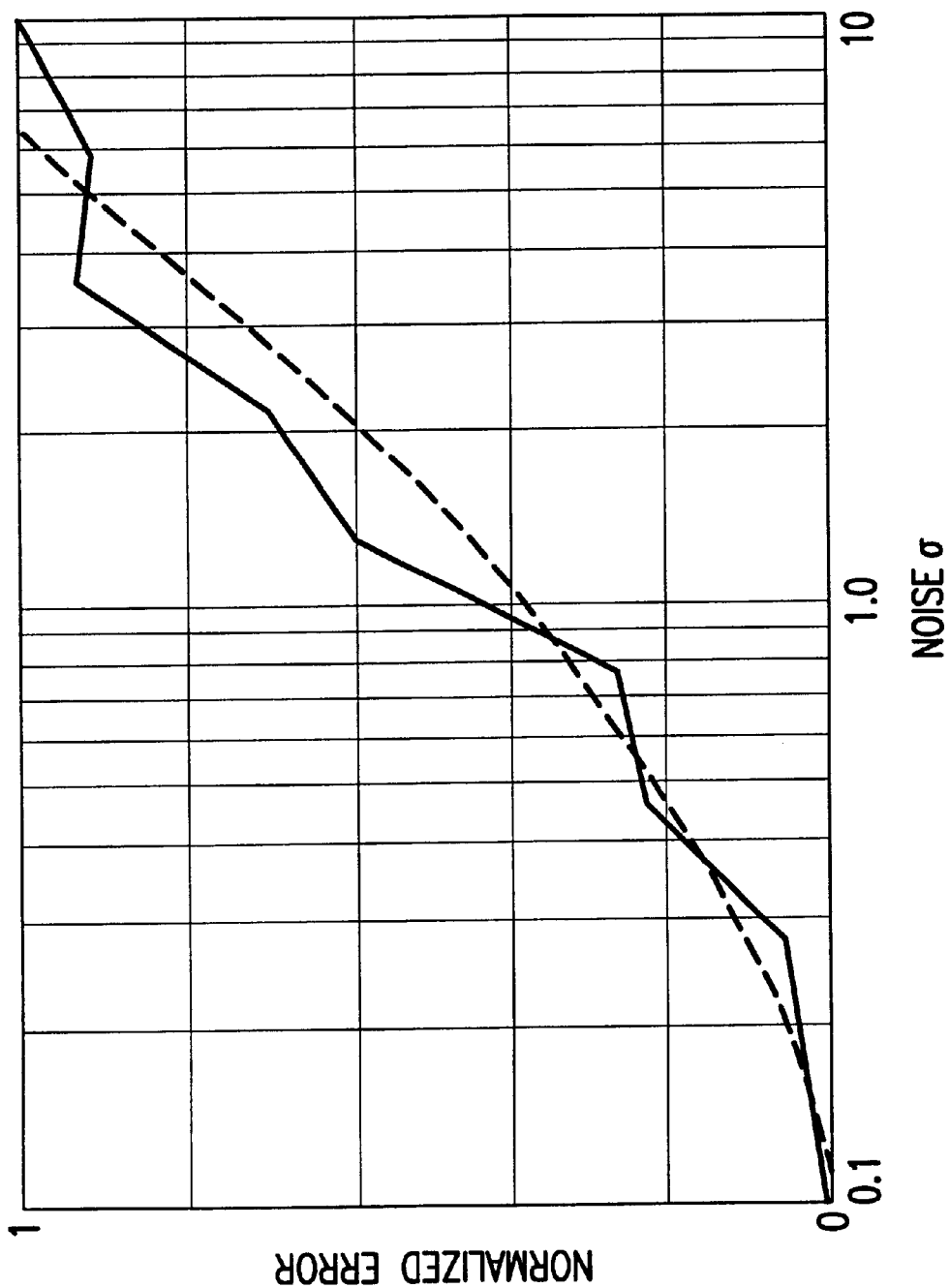
FIG. 2 shows the normalized error between fast $T_2$ components (0.5 to 3 ms) and the input model as a function of noise.
Figure 3:
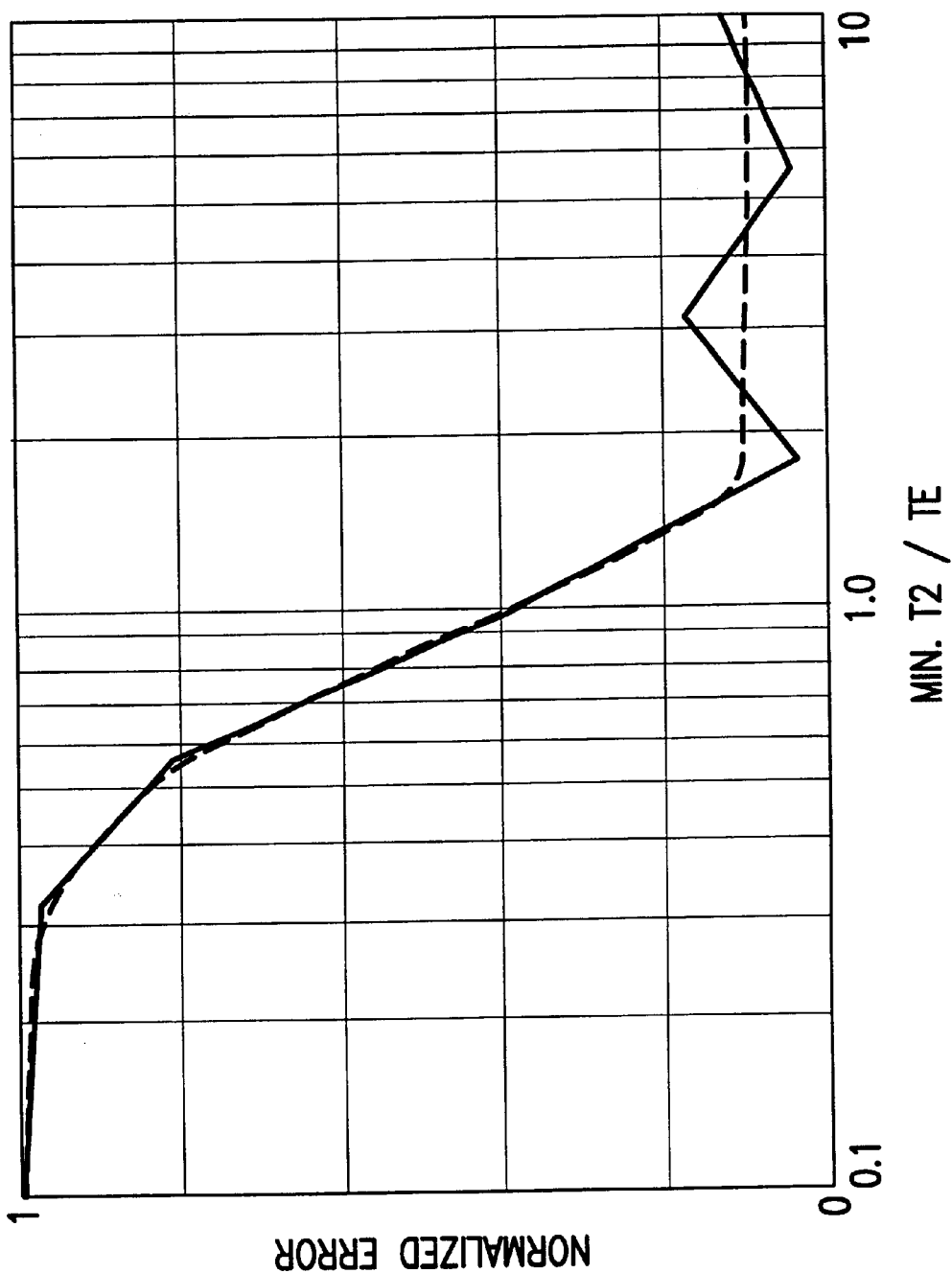
FIG. 3 shows modeling results in terms of a normalized error.

In accordance with the present invention, in order to obtain a $T_2$ spectrum of the NMR signal with optimized resolution over a geologically meaningful range of values it is proposed to combine time-domain input signals with different parameters optimized to cover different portions of the corresponding $T_2$ spectrum. Furthermore, in accordance with the present invention to overcome uncertainties associated in the prior art with the selection of a "combining point", and to be able to process different pulse-echo trains in a consistent manner, a novel method for combination of the input signals is proposed. In particular, in accordance with this invention, instead of inverting the separate echo trains data separately and merging the spectra later, the different raw pulse-echo data trains are used to construct a single echo train.

In a preferred embodiment, the input echo trains can be acquired with different $T_e$, $T_w$, and signal-to-noise ratio (SNR) parameters using, for example, NUMAR's MRIL® tool, D series. By combining two or more echo trains with different $T_e$ and SNR, in accordance with the present invention a single resulting echo train can be composed, which is optimized in terms of $T_2$ resolution. This echo train serves as input for $T_2$ inversion algorithms, that can handle echo trains with different $T_e$ and SNR, such as the MAP algorithm (Prammer et al., paper SPE 28368). For details in the implementation of the MAP algorithm, the reader is directed to the disclosure in the concurrently pending application Ser. No. 08/816,395 to one of the co-inventors, the content of which is incorporated herein by reference for all purposes.

Specifically, in a preferred embodiment, the resulting echo train is composed of "chunks" of input data optimized with regard to the length, inter-echo spacing and noise (i.e., "$T_2$ resolving power"). In a specific embodiment, the combined echo train consists of approximately 10–20 highly stacked, very low noise echoes with $T_e$ approximately equal to 0.6 ms, followed by about 50 echoes with stacked, low noise data (having $T_e$ approximately equal to 1.2 ms) and several hundred unstacked echoes ($T_e$=1.2 ms). In accordance with the present invention, a $T_2$ spectrum calculated from such echo data has an error function that is equally distributed over the entire distribution.

As recognized in the art, the most efficient way to record stacked echo trains is to acquire partially recovered data. Hence, the amplitudes of the different input echo train data sets differ. Therefore, in accordance with another aspect of the present invention, before combining the different data sets, amplitude matching is applied. In a specific embodiment in which the recovery spectrum (i.e., $T_1$ distribution) is known or can be determined with sufficient accuracy, the partially recovered echoes can be accurately corrected. In accordance with the present invention this correction can be performed using, for example, the method disclosed by Dunn et al. (see the corresponding reference above, paper JJ, May 1998). The Dunn et al. reference is hereby expressly incorporated by reference.

In accordance with preferred embodiments in which $T_1$ information is not available, the partially recovered data is matched amplitude-wise to the fully polarized echoes as disclosed in more detail below.

In particular, in a specific embodiment in which $T_1$ information is not available, the "missing" amplitude is determined statistically and then the full amplitude is reconstructed based on this information. A specific implementation of the method for amplitude matching is described below.

In accordance with a preferred embodiment, if the input echo trains are acquired with $T_w$ too short to allow the protons to fully polarize (i.e., with partial recovery), the respective amplitude has to be adjusted to match the fully recovered echo data. The amount of amplitude adjustment provides information about $T_1$.

Described below is an application and implementation of the method in accordance with the present invention. For the sake of specificity, a typical example is provided using the "total porosity" measurement as described by Prammer et al. (see above reference to paper SPE 36522).

A short, partially recovered echo train (Length=6 ms, $T_e$=0.6 ms and $T_w$=20 ms, in the sequel denoted "PR"), having high SNR is acquired together with a long, fully recovered echo train (Length=400–500 ms, $T_e$=1.2 ms and $T_w$=8000 s, further denoted "FR"). The partially recovered echo train has lower amplitude, depending on the wait-time $T_w$ and $T_1$ distribution.

Figure 4:
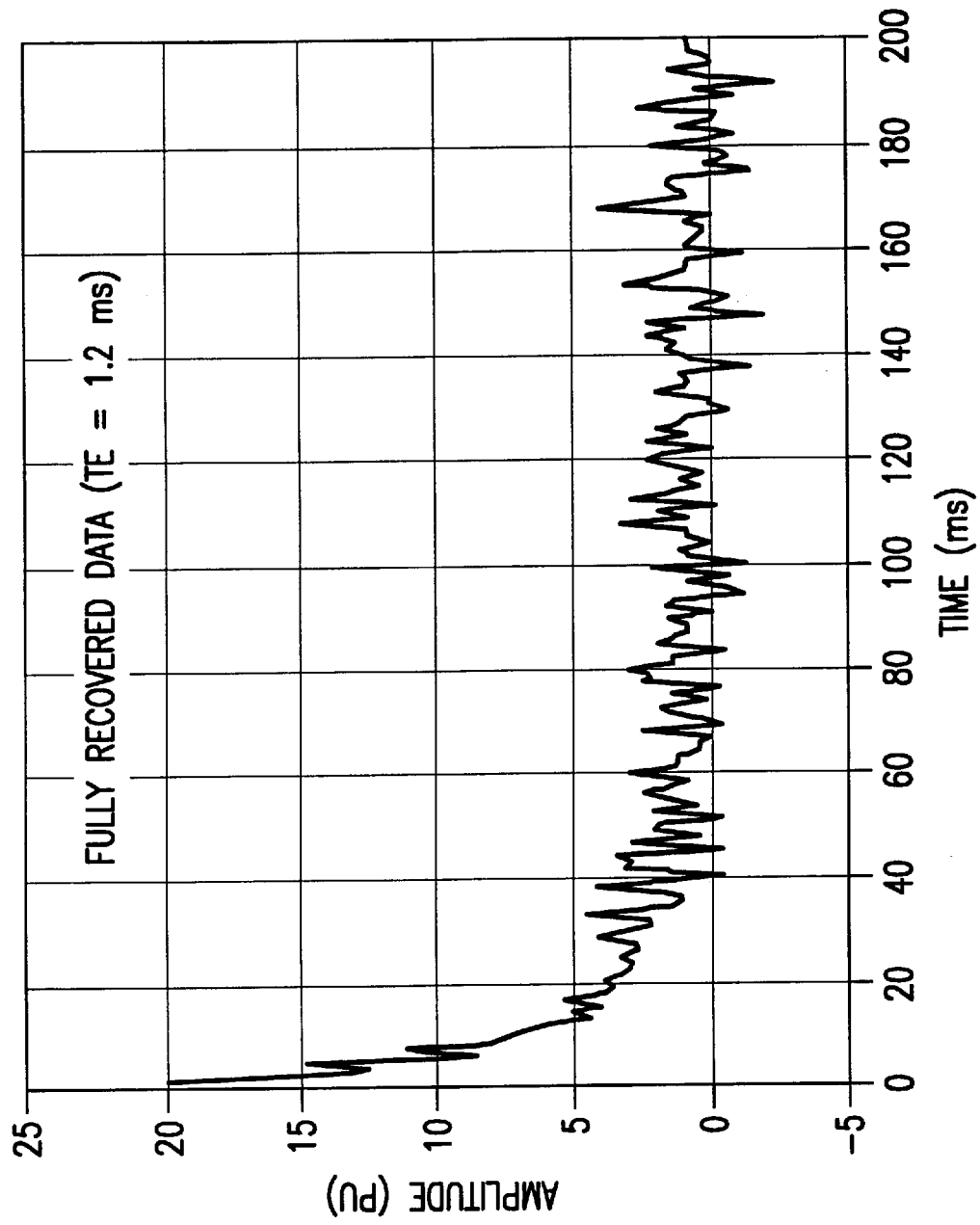
FIG. 4 shows a fully recovered echo train, $T_e$=1.2 ms, $T_w$=8000 ms, raw data.
Figure 5:
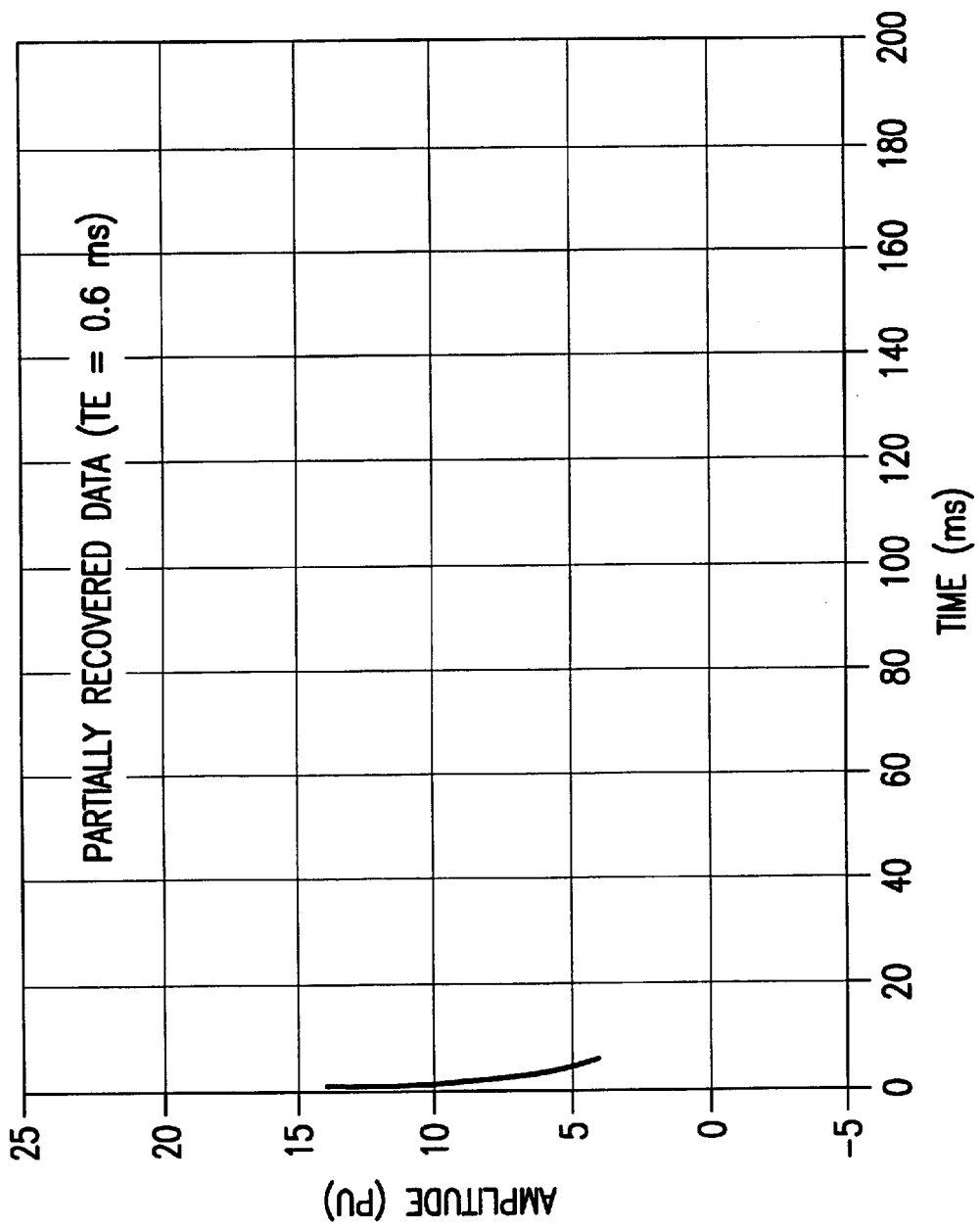
FIG. 5 shows a partially recovered echo train, $T_e$=0.6 ms, $T_w$=20 ms, raw data.
Figure 6:
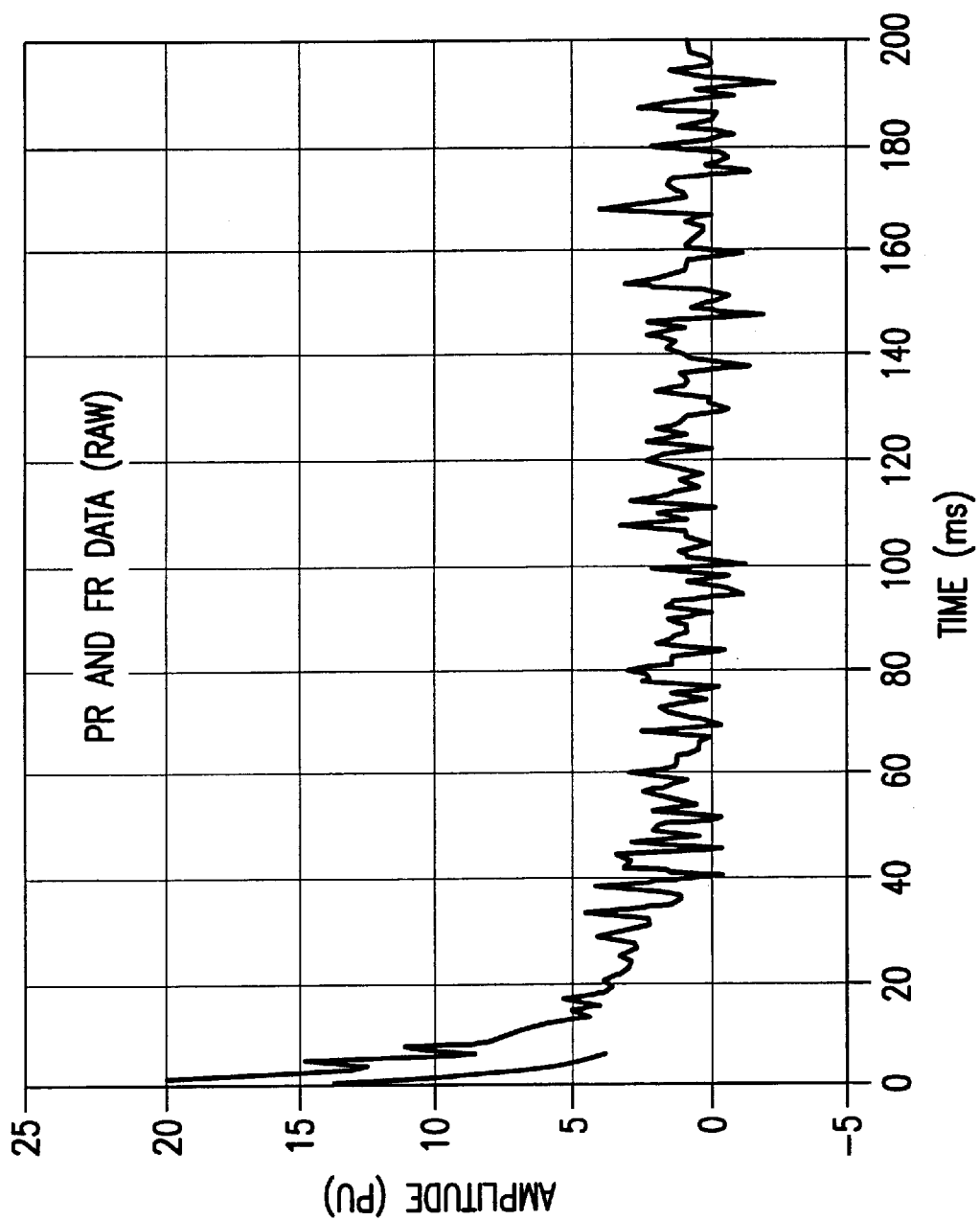
FIG. 6 shows a comparison of partially and fully recovered echo trains, raw data, illustrating the amplitude difference between the partially recovered (PR) and the fully recovered (FR) data; the PR data exhibits much lower noise.

By means of illustration, FIG. 4 shows the first 200 ms of a fully recovered echo train, raw data having respectively $T_e$=1.2 ms and $T_w$=8000 ms. FIG. 5 shows a partially recovered echo train, $T_e$=0.6 ms, $T_w$=20 ms, raw data. FIG. 6 shows a comparison of partially and fully recovered echo trains, raw data, illustrating the amplitude difference between the partially recovered (PR) and the fully recovered (FR) data. The PR data exhibits considerably lower noise.

In accordance with a specific embodiment of the present invention, one possibility to correct the PR-data for the "missing" amplitude is to separately calculate appropriate $T_2$ spectra for the PR and the FR echo trains. The difference between the two spectra indicates the "missing" amplitude. The back-transform of the difference into time domain yields an artificial exponentially decaying "echo train" which, when added to the original PR echo train, adjusts the PR data amplitude to the FR data amplitude. Note that this correction is a linear operation that does not change the noise characteristics of the PR data. This is important since any change in noise distribution would violate the assumption that the noise distribution is Gaussian, which is used by most $T_2$ inversion algorithms. In accordance with this embodiment, a-priori $T_1$ information is not required to correct the PR echo train. The "missing" amplitude is directly determined from $T_2$ spectra of each echo train (PR and FR).

Figure 7:
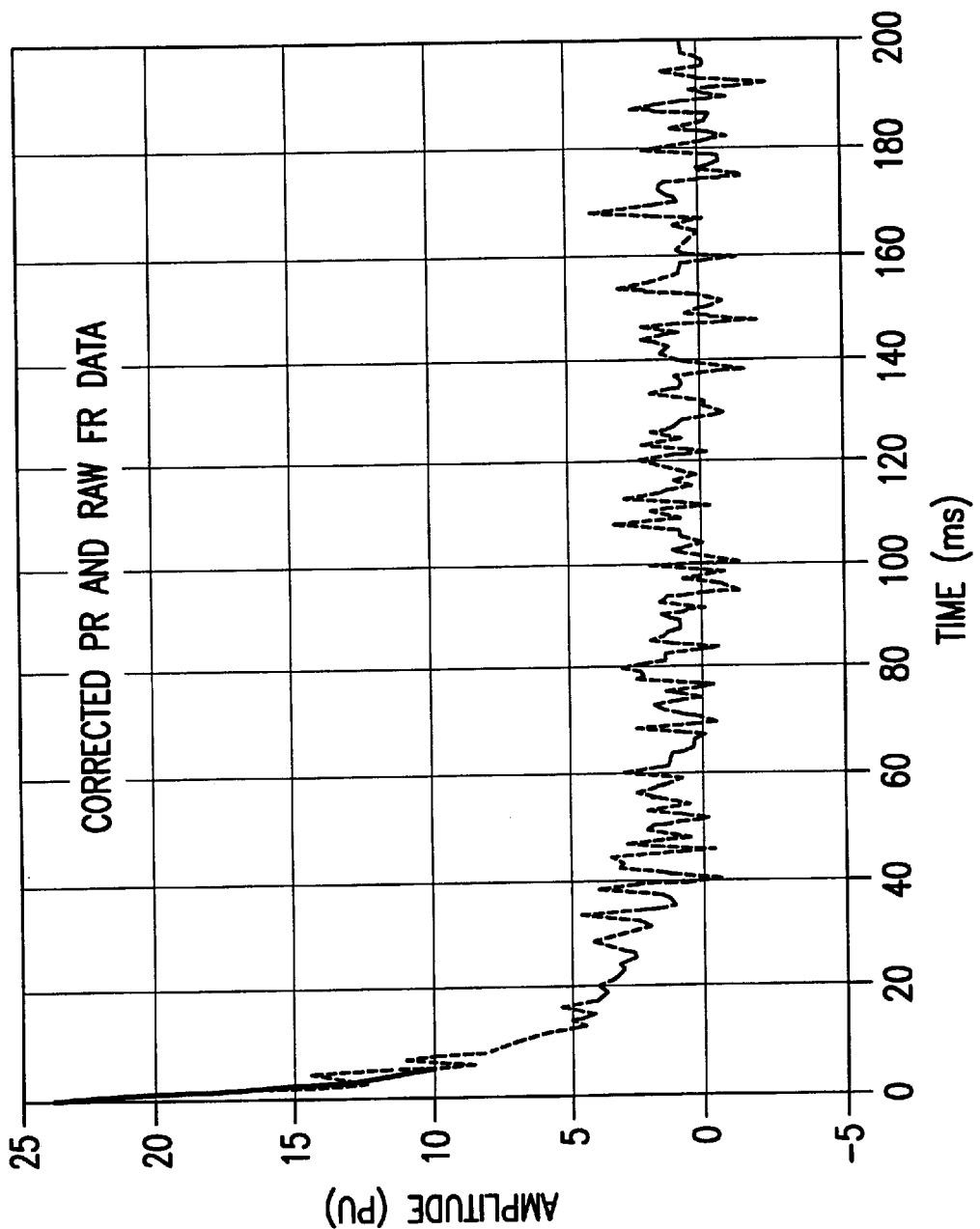
FIG. 7 shows raw, corrected, partially and fully recovered echo trains in which the amplitude of the PR echo train matches the FR data.
Figure 8:
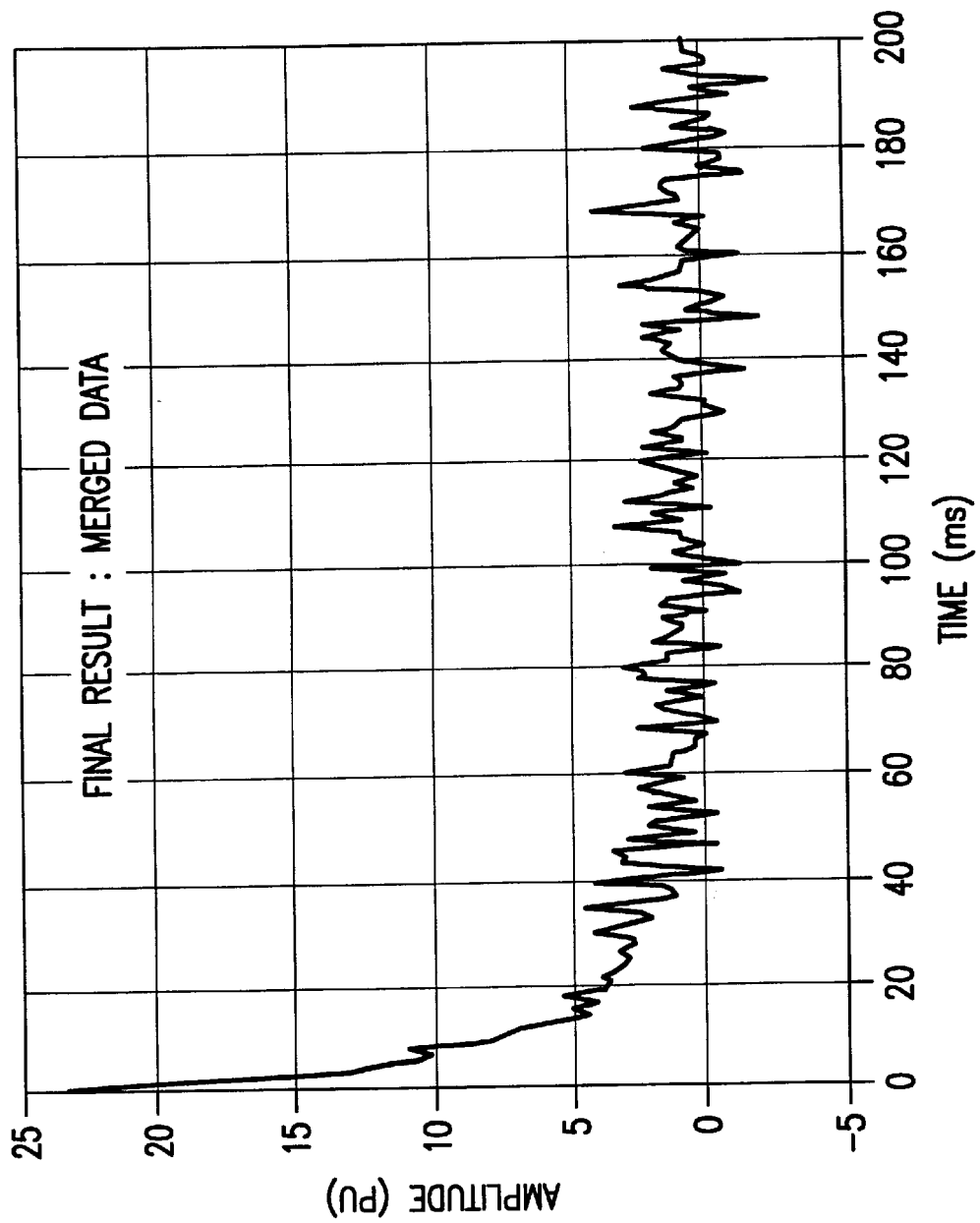
FIG. 8 shows the final result, merged data in accordance with the present invention—time section 0.6–6 ms has a $T_e$=0.6 ms with very low noise; the rest of the merged echo train has a $T_e$=1.2 ms.

FIG. 7 shows raw, corrected, partially and fully recovered echo trains in which the amplitude of the PR echo train matches the FR data. FIG. 8 shows the final result of the application of the method of the present invention: merged data in which time section 0.6–6 ms has a $T_e$=0.6 ms with very low noise; the rest of the merged echo train has a $T_e$=1.2 ms.

THE METHOD

Following is a specific implementation of the amplitude correction and merging method of NMR echo trains, in accordance with a preferred embodiment of the present invention. As noted above, to match the partially recovered data (PR) amplitude-wise with the fully recovered echo train (FR), the amount of "missing" amplitudes has to be determined. Based on the assumption that fast $T_2$ components are fully recovered even in the PR data and that only medium and slow $T_2$ components are too small, the following steps are used for the merging of PR with FR echo train data in accordance with a preferred embodiment.

1. In the first step of the method, input data including partially recovered (PR) and fully recovered (FR) data is inverted using any algorithm capable of handling echo trains with different $T_e$ and SNR parameters, such as the MAP algorithm proposed by one of the co-inventors of the present invention. For details of the MAP method the reader is referred to application Ser. No. 08/816,395, the content of which is incorporated herein by reference for all purposes. With reference to the notations introduced above, in this step PR06 and FR12 data is inverted using, for example, the MAP algorithm (see also Prammer paper SPE 28368 for further detail).

The selection of the fastest and longest $T_2$ bin for the PR data is based on the criteria outlined above. An typical echo train with $T_e$=0.6 ms and length 6 ms, for instance, is inverted in accordance with a preferred embodiment of the present invention with 0.5, 1, 2, 4, 8, 16 and 256 ms bins. The 256 ms bin accounts for any baseline offsets.

For a typical FR echo train, (a 1.2 ms/480 ms data set) in a preferred embodiment the bins are selected as follows: $bins_{FR}$=1, 2, 4, 8, 16, ... 1024 ms. The inversion of the PR and FR data yields two spectra, APR and AFR, respectively, which in a preferred embodiment are stored in a computer memory.

2. In the second step of the process, the difference between $A_{PR}$ and $A_{FR}$ is calculated for all bins within certain range. In the specific embodiment discussed above, the difference is calculated for all bins >8 ms.

In an alternate embodiment, the method involves calculating a bi-exponential curve using the differences of the 4 and 8 ms bins from PR and FR data and further involves calculating the amplitude difference of the sum of FR-bins 32–1024 ms, and PR-bin 256 ms.

Following these calculations, in accordance with a preferred embodiment, an "artificial" echo train calculated as described below is added to the original PR echo train. This operation can be expressed for a specific embodiment considered above using the following pseudo-code:

For each bin i with $T_2$=(8, 16, 256 ms) add
 $(A_{FR}(i)-A_{PR}(i))*\exp(-t_{PR}/bins(i))$ to PR data.

The above computation can be expressed more generically as follows:

For each $T_2$ spectrum bin i with $T_2$=($\alpha$, ..., $\omega$ ms) add
 $(\Delta A(i))*\exp(-t_i/bins(i))$ to said at least one first echo train;

where $\alpha$, ..., $\omega$ are bins in the $T_2$ spectrum range; $t_1$ corresponds to echo time of the first echo train; and $\Delta A(i)$ is a $T_2$ spectrum amplitude difference between said at least one first echo train and said at least one second echo train in the i-th bin.

In accordance with the present invention this step yields an amplitude corrected PR echo train $PR_{cor}$.

3. In the third step of the method, $PR_{cor}$ and FR12 data is merged. In a specific embodiment the step involves, taking the first 6 ms from the $PR_{cor}$ and the rest from the FR data, yielding the final echo train $ET_{merged}$ signal. An example of such a merged signal is illustrated in FIG. 8.

4. In the fourth and last step of the method, $ET_{merged}$ data is provided as an input for standard $T_2$ inversion.

It should be noted that only linear operations are applied to the PR echo train, so that the character of the noise is not affected. This feature is believed to provide significant advantages over alternative merging methods.

A person of skill in the art would appreciate that it would be a straightforward extension of the method to combine more than two echo trains, possibly corresponding to more than two regions of the $T_2$ spectrum. For example, instead of a single partially recovered and a single fully recovered regions, one can subdivide the spectrum into more than two regions, and then use pulse echo sequences optimized for each individual subdivision. As before, amplitude correction can be applied, if necessary, prior to merging of the echo trains in the time domain into a single echo train. The reader is directed to the bottom track in FIG. 9 for an illustration of the method.

Further examples illustrating the application of the proposed method are discussed in more detail below.

Field Examples

All data presented in this section were recorded with NUMAR's MRIL Series D tool. This new multi-volume logging tool has the capability to record multiple experiments simultaneously.

Figure 9A:
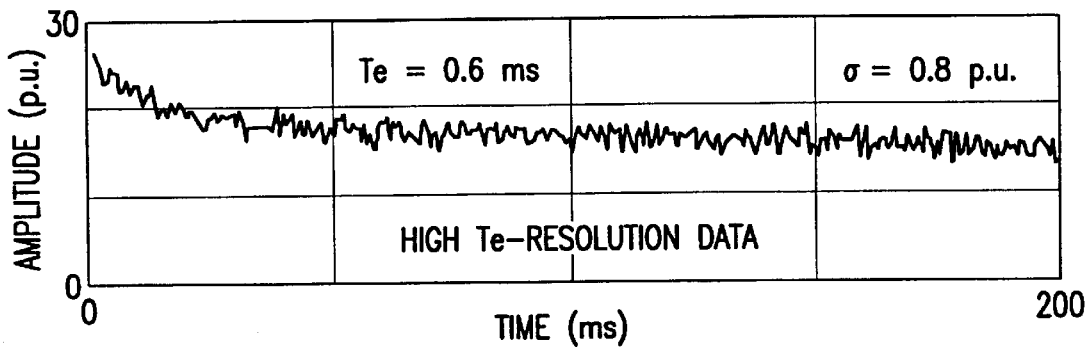
FIG. 9 shows data recorded in a test well in Malvern, Pa.
Figure 9B:
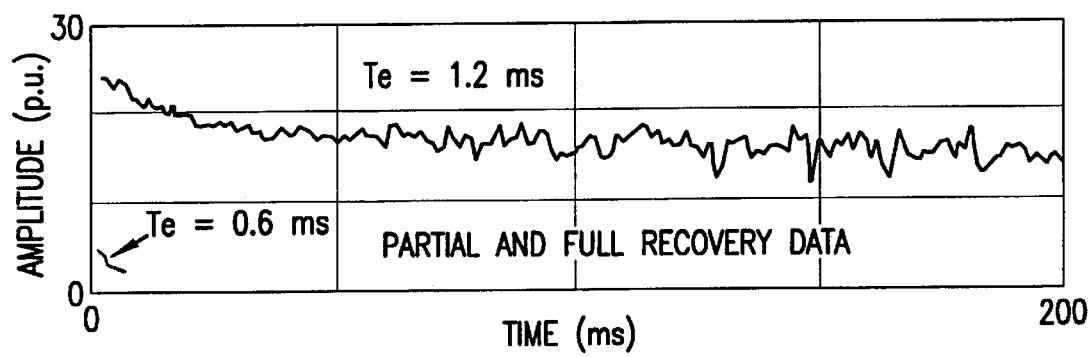
Figure 9C:
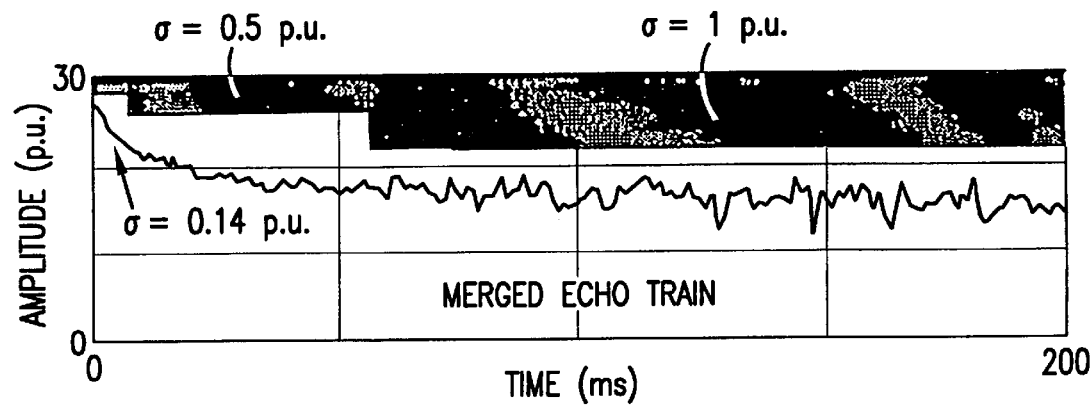

The first example shown in FIG. 9 was recorded in NUMAR's test well in Malvern, Pa. The data was acquired in a block of Torrey Buff sandstone with bulk water above the rock. The top graph presents a 480 ms long echo train with $T_e$=0.6 ms ("High Te-Resolution Data"). Note that although the echo train is 480 ms long, only the first 200 ms are shown for the sake of visual resolution. The wait-time of Tw=8000 ms between measurements allows the hydrogen to fully repolarize. A total of 8480 ms are required to record one of these echo trains. Assuming a four-fold stack to enhance the signal-noise-ratio, a single-volume NMR logging requires almost 34 s resulting in unacceptably low logging speed.

The center graph in FIG. 9 ("Partial & Full Recovery Data") shows two echo trains. The first echo train is a 6 ms short, under-polarized echo train with $T_e$=0.6 ms and Tw =20 ms. This echo train is heavily stacked resulting in a sevenfold noise reduction ($\sigma$=0.14). The second echo train shown in this graph is 480 ms long, full-recovered data with $T_e$=1.2 ms and Tw=8000 ms. Only the first 50 echoes (i.e, 60 ms) are stacked four-fold yielding $\sigma$=0.5, while the last 350 echoes (420 ms) are not stacked ($\sigma$=1.0). The total time required to measure this set of echo trains with a single-volume tool is still about 34 s, while the new MRIL Series D tool can perform the same task in about 8.5 s. Using the full technical capabilities of the Series D tool, two sets of these noise-optimized echo trains are simultaneously recorded. This yields a 14:1 noise reduction of the partial recovery data compared to a single echo train; a 4:1 noise reduction on the first 60 ms of the full recovery data and a 2:1 noise reduction on the remaining echoes. The multi-volume Series D tool needs about 17 s to record such data while single-volume mode would require 68 s.

The bottom graph in FIG. 9 presents merged partial and fall recovered data. This composite echo train is noise-optimized in terms of $T_2$ resolution as outlined above. The improvement in data quality is apparent. Compared to the 480 ms/$T_e$=0.6 ms data [top graph], particularly the first 60 ms exhibit reduced noise.

Figure 10:
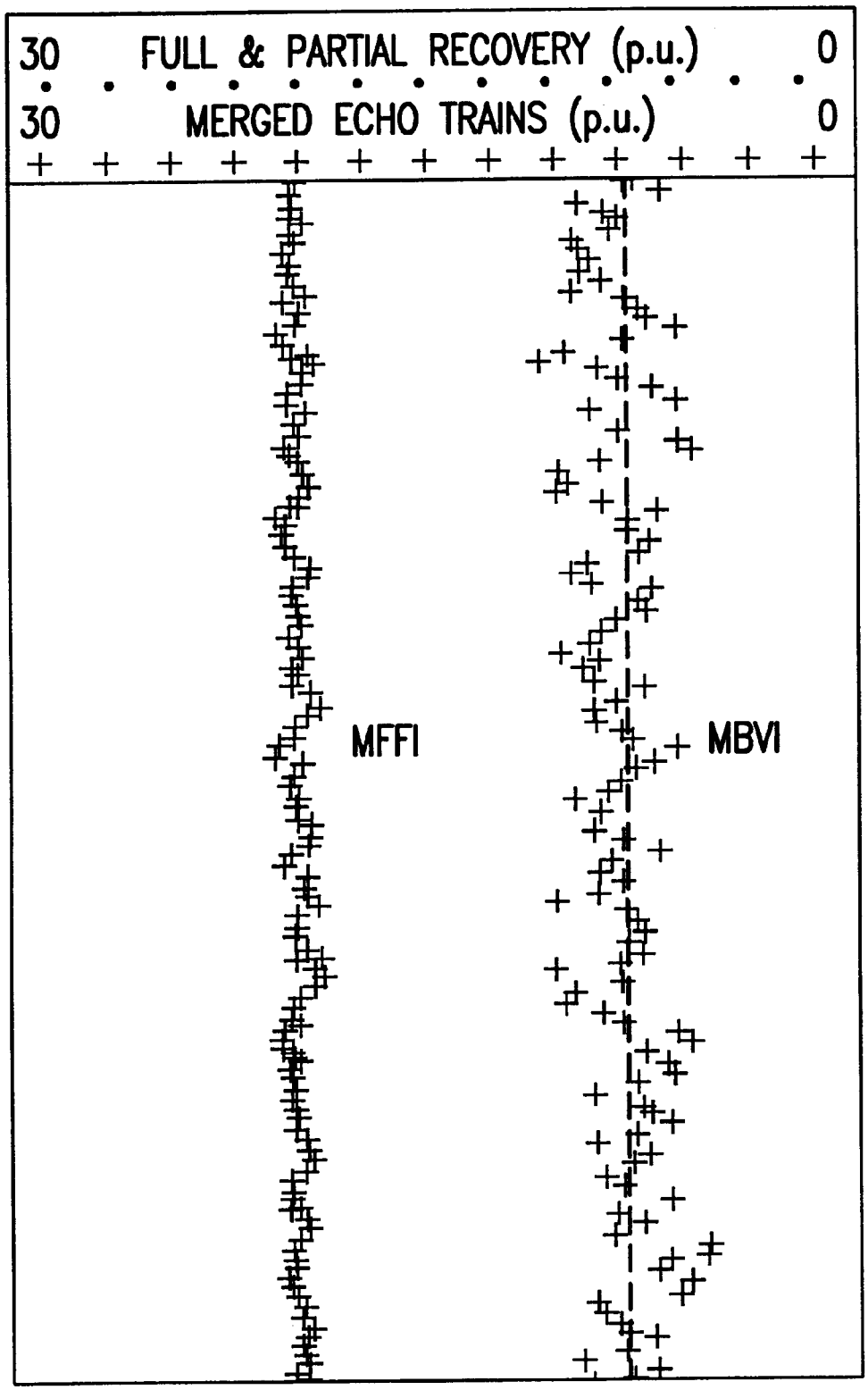
FIG. 10 illustrates analysis of the stationary data shown in detail in FIG. 9.

Table 1 presents bound-water related porosity MBVI and the Free Fluid Index MFFI and NMR Total Porosity MSIG calculated using the measurements described above. The respective logs are shown in FIG. 10.

TABLE 1

COMPARISON OF CONVENTIONAL AND NEW METHOD

| Porosity | High $T_e$-Resolution | Separate $T_2$-Inversion | Method Echo Trains |
|---|---|---|---|
| MSIG (p.u.) | 27.0 ± 1.1 | 27.6 ± 1.1 | 26.8 ± 1.1 |
| MFFI (p.u.) | 19.6 ± 0.4 | 19.7 ± 0.4 | 19.6 ± 0.4 |
| MBVI (p.u.) | 7.4 ± 1.1 | 7.9 ± 1.2 | 7.2 ± 1.2 |

Table 1 shows results from NUMAR's test well. The porosities in the left column ("High $T_e$-Resolution") were calculated from single echo trains with Ne=800 echoes and $T_e$=0.6 ms. The center column ("Separate $T_2$ Inversion") shows data determined by inverting the short partial and the long full recovery echo trains separately and combining the spectra. The porosities in the right column were calculated from merged echo trains using the method of the present invention. An Example of the input data is shown in FIG. 10.

As seen in the table, MFFI is in good agreement for all three methods. The respective standard deviation is 0.4 p.u. While MBVI from High $T_e$-Resolution data and Merged Echo Trains data yield almost the same result, MBVI determined by calculating the $T_2$ spectra separately reads about 0.5 p.u. too high. All three results agree, however, within the standard deviation of 1.1 p.u. and 1.2 p.u. respectively. The MBVI difference can be explained by the fact that, as outlined above, the fast $T_2$ components are sensitive to noise. The inversion of a short echo train is more prone to "pick-up" noise thus over-determining MBVI. Long $T_2$ components on the other hand are less sensitive to noise. Although the noise of the later echoes of the merged data (FIG. 9, bottom) is slightly higher than the High $T_e$-Resolution data noise (FIG. 9, top), the MFFI results (i.e., long $T_2$ components) are the same.

Since the results from the High $T_e$-Resolution data and the merged data are virtually the same, the logging speed advantage of multi-volume NMR logging tools can be fully exploited without compromising data quality.

Figure 11:
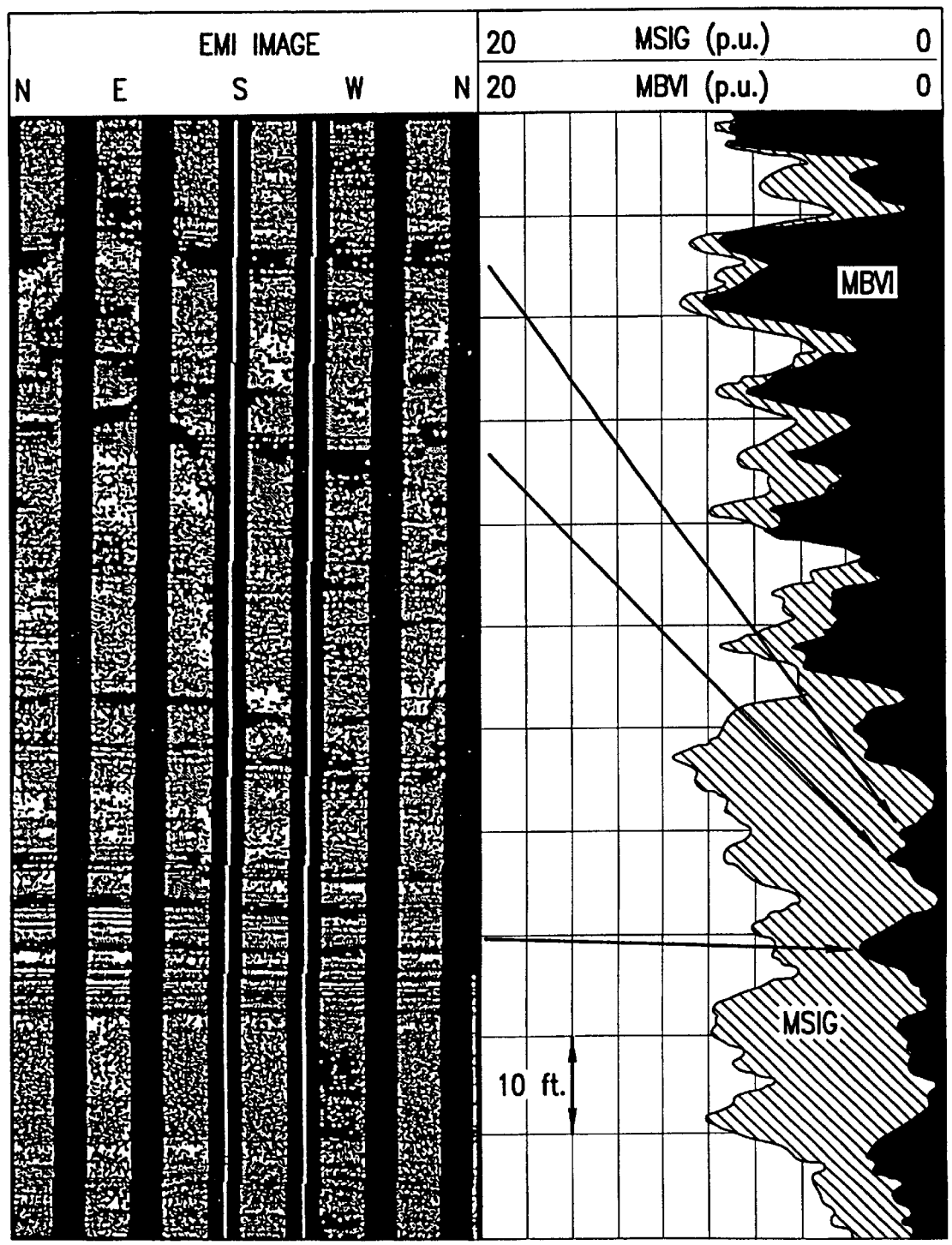
FIG. 11 is a comparison of EMI and MRIL logs from a Shell test facility at Johnson City, in a sandstone environment.
Figure 12:
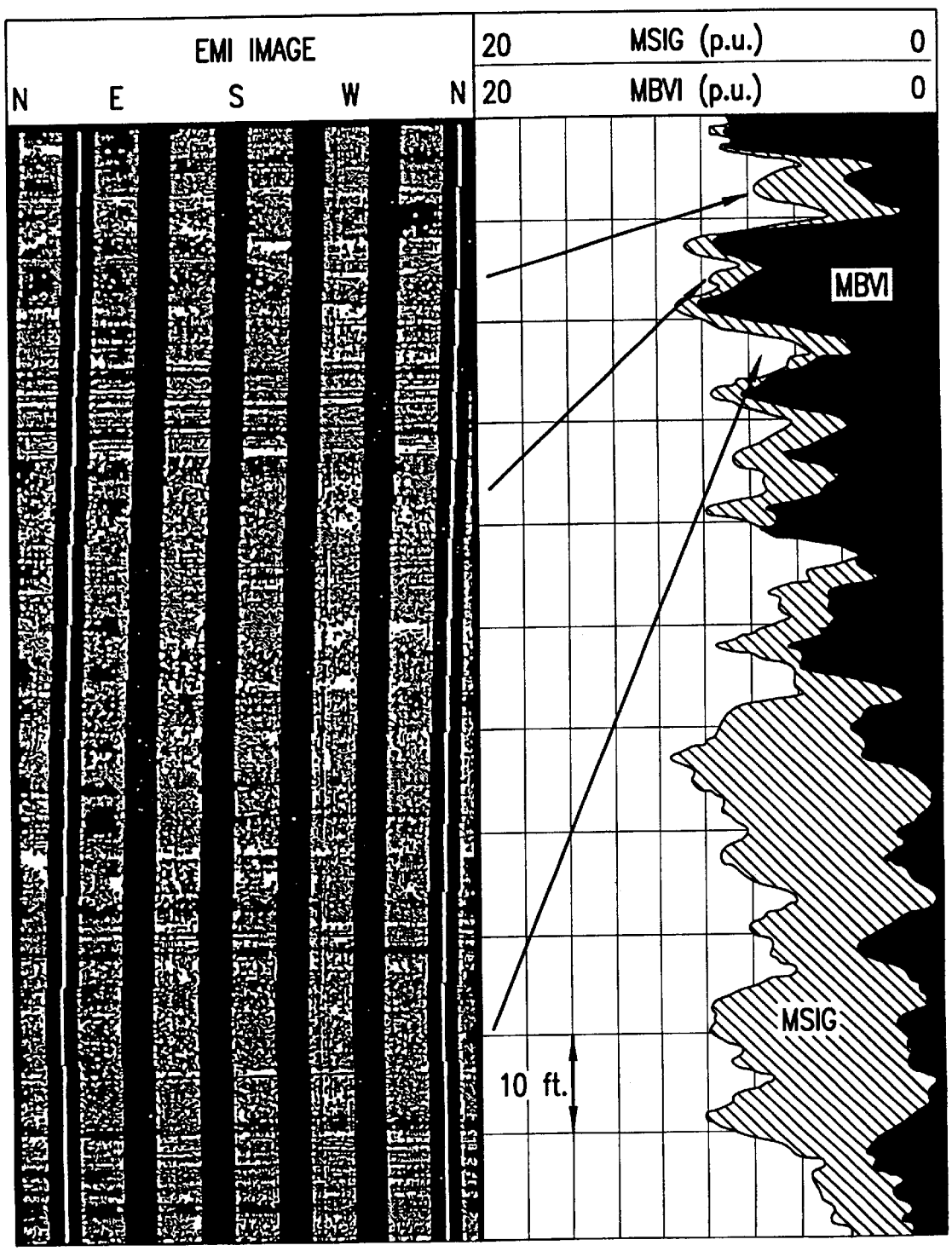
FIG. 12 is a comparison of EMI and MRIL logs from a Shell test facility at Johnson City, in a shale environment.

The second example was acquired at Shell's test facility at Johnson City. The logs were recorded in the lower part of the test well and are illustrated in FIG. 11 and FIG. 12. FIGS. 11 and 12 compare NMR Total Porosity MSIG and Bulk Water irreducible MBVI calculated from merged echo trains with the EMI® log (EMI® is a mark of Halliburton). FIG. 11 shows a section of the EMI® log recorded in the sands. As seen in the figure, the MRIL® logs, i.e., MBVI and MSIG, are in good agreement with the EMI image. Thin clay layers, indicated by dark stripes in the EMI image, can be identified by an increase in MBVI. The predominant sandstone beds exhibit low MBVI porosity and high MSIG. These beds appear in the EMI image from the shallow part of the well. This interval of the well is a thinly laminated sand—shale sequence. Again, EMI and MRIL logs are in good agreement. The arrows in FIG. 11 denote clay layers indicated by peaks in MBVI and dark stripes in the EMI image. The arrows in FIG. 12 point to sandstone layers, which exhibit low MBVI and have a "grainy" appearance in the EMI image.

For the reader's convenience, attached below is the nomenclature used in the above disclosure.

MBVI=NMR bulk water irreducible, p.u.
MFFI=NMNR free fluid index, p.u.
MSIG=NMR total porosity, p.u.
Ne=number of echoes
$T_1$=longitudinal NMR relaxation time, s
$T_2$=transversal NMR relaxation time, s
$T_e$=inter-echo spacing, ms
$T_w$=wait time, s
σ=noise standard deviation, p.u.

While the foregoing has described and illustrated aspects of various embodiments of the present invention, those skilled in the art will recognize that alternative components and techniques, and/or combinations and permutations of the described components and techniques, can be substituted for, or added to, the embodiments described herein. It is intended, therefore, that the present invention not be defined by the specific embodiments described herein, but rather by the appended claims, which are intended to be construed in accordance with the following well-settled principles of claim construction: (a) Each claim should be given its broadest reasonable interpretation consistent with the specification; (b) Limitations should not be read from the specification or drawings into the claims (e.g., if the claim calls for "antenna", and the specification and drawings show a coil, the claim term "antenna" should not be limited to a coil, but rather should be construed to cover any type of antenna); (c) The words "comprising", "including", and "having" are always open-ended, irrespective of whether they appear as the primary transitional phrase of a claim or as a transitional phrase within an element or sub-element of the claim; (d) The indefinite articles "a" or "an" mean one or more; where, instead, a purely singular meaning is intended, a phrase such as "one", "only one", or "a single", will appear; (e) Words in a claim should be given their plain, ordinary, and generic meaning, unless it is readily apparent from the specification that an unusual meaning was intended; (f) an absence of the specific words "means for" connotes applicants' intent not to invoke 35 U.S.C. §112 (6) in construing the limitation; (g) Where the phrase "means for" precedes a data processing or manipulation "function," it is intended that the resulting means-plus-function element be construed to cover any, and all, computer implementation(s) of the recited "function"; (h) a claim that contains more than one computer-implemented means-plus-function element should not be construed to require that each means-plus-function element must be a structurally distinct entity (such as a particular piece of hardware or block of code); rather, such claim should be construed merely to require that the overall combination of hardware/firmware/software which implements the invention must, as a whole, implement at least the function(s) called for by the claim's means-plus-function element(s); (i) a means-plus-function element should be construed to require only the "function" specifically articulated in the claim, and not in a way that requires additional "functions" which may be described in the specification or performed in the preferred embodiment(s); (j) The existence of method claims that parallel a set of means-plus-function apparatus claims does not mean, or suggest, that the method claims should be construed under 35 U.S.C. §112 (6).

What is claimed is:

1. A method for conducting NMR logging measurements, comprising:
    (a) providing at least one first echo train acquired using a first set of echo train parameters, said at least one first echo train carrying information concerning a first type of NMR signals;
    (b) providing at least one second echo train acquired using a second set of echo train parameters, said at least one second echo train carrying information concerning a second type of NMR signals having relaxation characteristics relatively slow compared with the first type of NMR signals;

(c) computing an artificial, exponentially decaying third echo train based on information concerning the first and second type of NMR signals:

(d) merging said at least one first and said at least one second echo trains in the time domain to obtain a merged echo train carrying information concerning both the first and the second type of NMR signals, said merging step comprising amplitude adjusting of said at least one first echo train to said at least one second echo train using the computed, exponentially decaying third echo train.

2. The method of claim 1 wherein said first echo train corresponds to partially recovered NMR signals.

3. The method of claim 1 wherein said second echo train corresponds to fully recovered NMR signals.

4. The method of claim 1 wherein said first and said second set of parameters comprises $T_e$ and signal-to-noise ratio (SNR) parameters.

5. The method of claim 1, wherein the inter-echo spacing $T_e$ used in the first set of parameters is different from the inter-echo spacing $T_e$ used in the second set of parameters.

6. The method of claim 1, wherein parameters of said at least one first echo train and said at least one second echo train are selected to optimize the $T_2$ resolution of the merged signal.

7. The method of claim 1 wherein the step of amplitude adjusting is performed using information about the $T_1$ spectrum of the signal.

8. The method of claim 7 wherein information about the $T_1$ spectrum of the signal is provided externally.

9. The method of claim 1 further comprising: inverting the merged echo train to obtain information about the properties of an underlying material and displaying said information in humanly-readable form.

10. The method of claim 1, wherein the step of computing comprises:
inverting said at least one first and said at least one second echo trains into the $T_2$ spectrum domain to obtain a first and second $T_2$ spectrum signals;
calculating the difference between the first and the second $T_2$ spectrum signals within a predetermined $T_2$ spectrum range; and
computing the third echo train used in the amplitude adjustment by inverting the difference between the first and the second $T_2$ spectrum signals within the predetermined $T_2$ spectrum range.

11. The method of claim 1 wherein said at least one first echo train and said least one second echo train are acquired quasi-simultaneously.

12. The method of claim 1 wherein said at least one first echo train and said least one second echo train are acquired in different sensitive volumes.

13. A method for conducting NMR logging measurements with enhanced transform domain resolution, comprising:
providing two or more NMR echo trains, each of said echo trains having parameters selected to cover a portion of the $T_2$ spectrum;
computing at least one artificial, exponentially decaying third echo train based on the provided two or more NMR echo trains or $T_1$ information;
combining said two or more NMR echo trains in the time domain into a merged echo train, the step of combining comprising amplitude adjusting said two or more NMR echo trains using the at least one computed, exponentially decaying third echo train; and
inverting the merged echo train to the $T_2$ spectrum domain to obtain information about the properties of an underlying material.

14. The method of claim 13 wherein at least one of said two or more NMR echo trains corresponds to partially recovered NMR signals and at least one of said two or more NMR echo trains corresponds to fully recovered NMR signals.

15. The method of claim 13 wherein parameters of said echo trains are optimized to enhance the transform domain resolution of the selected portion of the $T_2$ spectrum.

16. The method of claim 13, wherein the third echo train is computed based on a $T_2$ spectrum difference between said at least one first NMR echo train and said at least one second NMR echo train.

17. The method of claim 13, wherein the merged echo train comprises a combination of at least one first echo train amplitude adjusted using said third echo train with a second echo train.

18. The method of claim 13 wherein the step of amplitude adjusting is performed using information about the $T_1$ spectrum of the signal.

19. The method of claim 18 wherein information about the $T_1$ spectrum of the signal is provided externally.

20. The method of claim 13 wherein said parameters selected to cover a portion of the $T_2$ spectrum comprise $T_e$ and SNR parameters.

21. The method of claim 1 wherein at least two of said two or more NMR echo trains are acquired quasi-simultaneously.

22. The method of claim 13 wherein at least two of said two or more NMR echo trains are acquired in different sensitive volumes.

23. A method of operating a multi-volume NMR logging tool, comprising:
(a) acquiring a first NMR echo train or sets of echo train in a first sensitive volume of the tool, said first echo train(s) carrying information concerning a first type of NMR signals;
(b) acquiring a second NMR echo train or sets of echo trains in a second sensitive volume of the tool, said second echo train(s) carrying information concerning a second type of NMR signals having relaxation characteristics relatively slow compared with the first type of NMR signals;
(c) computing an artificial, exponentially decaying third echo train based on information concerning the first and second type of NMR signals: and
(d) merging said first and said second echo train(s) in the time domain to obtain a merged echo train carrying information concerning both the first and second type of NMR signals, said merging step comprising amplitude adjusting said at least one first echo train to said at least one second NMR echo train using the computed, exponentially decaying third echo train.

24. The method of claim 23 wherein said first echo train(s) and said second echo train(s) are acquired quasi-simultaneously.

25. The method of claim 23 wherein said first echo train(s) correspond to partially recovered NMR signals.

26. The method of claim 23, wherein the merged echo train comprises a combination of the second echo train with the amplitude adjusted first echo train.

27. The method of claim 25, wherein the merged echo train comprises a portion of the second echo train appended to the amplitude adjusted first echo train.

28. The method of claim 26 wherein the step of adjusting is performed using information about the $T_1$ spectrum of the signal.

29. The method of claim 28 wherein information about the $T_1$ spectrum of the signal is provided externally.

30. An apparatus for conducting NMR logging measurements, comprising:
- (a) means for providing at least one first echo train acquired using a first set of echo train parameters, said first echo train carrying information concerning a first type of NMR signals;
- (b) means for providing at least one second echo train acquired using a second set of echo train parameters, said second echo train carrying information concerning a second type of NMR signals having relaxation characteristics relatively slow compared with the first type of NMR signals;
- (c) means for computing an artificial, exponentially decaying third echo train based on information concerning the first and second type of NMR signals:
- (d) means for merging said at least one first and said at least one second echo trains in the time domain to obtain a merged echo train carrying information concerning both the first and the second type of NMR signals, said means for merging receiving input from said means for computing; and
- (e) means for processing the merged echo train to derive properties of a material being investigated.

31. The apparatus of claim 30 further comprising means for acquiring NMR echo trains in two or more sensitive volumes.

32. The method of claim 10, wherein the difference between the first and the second $T_2$ spectrum signals is calculated over the range $T_2=(8, 16, 256$ ms$)$.

33. The method of claim 1, wherein amplitude adjusting is computed using the formula:

For each $T_2$ spectrum bin i with $T_2=(\alpha, \ldots, \omega$ ms$)$ add $(\Delta A(i))^*\exp(-t_1/\text{bins}(i))$ to said at least one first echo train;

where $\alpha, \ldots,$ are bins in the $T_2$ spectrum range; $t_1$ corresponds to echo time of the first echo train; and $\Delta A(i)$ is a $T_2$ spectrum amplitude difference between said at least one first echo train and said at least one second echo train in the i-th bin.

34. The method of claim 33, wherein the variable difference $\Delta A$ is computed using information about the $T_1$ spectrum of the signal.

35. The method of claim 33, wherein the $T_2$ spectrum bins are in the range $T_2=(8, 16, 256$ ms$)$.

36. The method of claim 1, wherein the merged echo train comprises a combination of the second echo train with the amplitude adjusted first echo train.

37. The method of claim 36, wherein the merged echo train comprises a portion of the second echo train appended to the amplitude adjusted first echo train.

38. The method of claim 36, wherein the merged echo train comprises the second echo train appended to a portion of the amplitude adjusted first echo train.

39. The method of claim 17, wherein the merged echo train comprises a portion of the second echo train appended to the amplitude adjusted first echo train.

40. The method of claim 17, wherein the merged echo train comprises the second echo train appended to a portion of the amplitude adjusted first echo train.

41. The method of claim 25, wherein the merged echo train comprises the second echo train appended to a portion of the amplitude adjusted first echo train.

42. The method of claim 13, wherein parameters of said two or more NMR echo trains are selected to optimize the $T_2$ resolution of the merged signal.

43. The method of claim 23, wherein parameters of said first echo train and said second echo train are selected to optimize the $T_2$ resolution of the merged signal.

44. The method of claim 42, wherein different portions of the $T_2$ spectrum of the merged signal exhibit different noise properties.

* * * * *